(12) United States Patent
Kim et al.

(10) Patent No.: US 11,643,645 B2
(45) Date of Patent: May 9, 2023

(54) NUCLEIC ACID EXTRACTION DEVICE AND OPERATING METHOD THEREFOR

(71) Applicant: MICO BIOMED CO., LTD., Seongnam-si (KR)

(72) Inventors: Sung Woo Kim, Seoul (KR); Eun Sub Kim, Bucheon-si (KR); Song Gyun Jung, Bucheon-si (KR); Jae Young Byun, Bucheon-si (KR); Duck Joong Kim, Anyang-Si (KR); Jin Pyung Kim, Seoul (KR)

(73) Assignee: MICO BIOMED CO., LTD., Seongnam-si (KR)

( * ) Notice: Subject to any disclaimer, the term of this patent is extended or adjusted under 35 U.S.C. 154(b) by 169 days.

(21) Appl. No.: 17/264,711

(22) PCT Filed: Jul. 31, 2019

(86) PCT No.: PCT/KR2019/009521
§ 371 (c)(1),
(2) Date: Jan. 29, 2021

(87) PCT Pub. No.: WO2020/027566
PCT Pub. Date: Feb. 6, 2020

(65) Prior Publication Data
US 2021/0301284 A1 Sep. 30, 2021

(30) Foreign Application Priority Data
Aug. 1, 2018 (KR) .......................... 10-2018-0090066

(51) Int. Cl.
*C12N 15/10* (2006.01)
*B01L 3/00* (2006.01)

(52) U.S. Cl.
CPC ........ *C12N 15/1003* (2013.01); *B01L 3/5027* (2013.01); *B01L 2200/0631* (2013.01); *B01L 2300/0627* (2013.01)

(58) Field of Classification Search
CPC ............... C12N 15/1003; B01L 3/5027; B01L 2200/0631; B01L 2300/0627; G01N 1/34;
(Continued)

(56) References Cited

U.S. PATENT DOCUMENTS

| 5,645,723 A | 7/1997 | Fujishiro et al. |
| 5,824,224 A * | 10/1998 | Fujishiro ................ B01D 61/18 210/473 |
| 2012/0121464 A1 | 5/2012 | Nogami et al. |

FOREIGN PATENT DOCUMENTS

| JP | 2014-194378 A | 10/2014 |
| JP | 2016-101178 A | 6/2016 |

(Continued)

*Primary Examiner* — Jennifer Wecker
*Assistant Examiner* — Oyeleye Alexander Alabi
(74) *Attorney, Agent, or Firm* — Bridgeway IP Law Group, PLLC; Sang Ho Lee; Hyun Woo Shin

(57) ABSTRACT

One aspect of the present invention provides a nucleic acid extraction device. The nucleic acid extraction device includes a container which stores each of a cleaning solution and an eluting solution, a water level sensor configured to detect amounts of the cleaning solution and the eluting solution which are stored in the container, a tube sensor configured to sense a sample tube disposed on a sample tube accommodation portion, and an operation initiation portion configured to determine whether the cleaning solution and the eluting solution which are necessary for a nucleic acid extraction operation are provided on the basis of the number of such sample tubes which is sensed by the tube sensor and the amounts of the cleaning solution and the eluting solution which are sensed by the water level sensor.

12 Claims, 11 Drawing Sheets

(58) Field of Classification Search
CPC .............. G01N 35/025; G01N 1/405; G01N 2035/0444; G01N 2035/1025; G01N 35/04; G01N 35/00722; G01N 2035/00178; G01N 2035/0441
See application file for complete search history.

(56) References Cited

FOREIGN PATENT DOCUMENTS

| | | |
|---|---|---|
| KR | 10-0968477 B1 | 7/2010 |
| KR | 10-2012-0079541 A | 7/2012 |
| WO | 97/32645 A1 | 9/1997 |

* cited by examiner

NUCLEIC ACID EXTRACTION DEVICE AND OPERATING METHOD THEREFOR

TECHNICAL FIELD

This application claims priority to and the benefit of Korean Patent Application No. 10-2018-0090066, filed on Aug. 1, 2018, the disclosure of which is incorporated herein by reference in its entirety.

The present invention relates to a nucleic acid extraction device and a method of operating the same, and more particularly, to a nucleic acid extraction device and a method of operating the same to be driven in a rotational manner to extract nucleic acid.

BACKGROUND ART

Polymerase chain reaction (PCR) for deoxyribonucleic acid (DNA) amplification, which is required as a necessary step in the field of biological research, needs a large amount of refined nucleic acid. Accordingly, a limitation occurs in manually separating, by a researcher, biological materials or nucleic acid in a university lab or an enterprise institute. To overcome the limitation, automation devices configured to extract a biological material or nucleic acid from a biological specimen have been manufactured and used.

As conventional methods for extracting nucleic acid, there are a method of separating adsorbed nucleic acid using a magnet such as magnetic beads, a method of pushing a solution by applying air to a column as a method of eluting a solution using a column, a method of eluting a solution by centrifugally separating a column itself, and the like.

However, automated nucleic acid extraction apparatuses using the above-described conventional methods have problems such as a relatively larger size and an excessive long specimen treatment time to treat a large number of specimens. Also, during a process of treating a large number of specimens, contamination caused by respective specimens may occur such that treatment efficiency is reduced and a user is inconvenienced.

Also, in general, to improve efficiency of nucleic acid extraction, a nucleic acid extraction operation was performed with respect to a plurality of samples for one cycle (one circulation). Here, since nucleic acid extraction is performed with respect to the plurality of samples, large amounts of a cleaning solution, an eluting solution, and the like were necessary for one cycle. When adequate amounts of the cleaning solution, the eluting solution, and the like were not provided, the nucleic acid extraction operation was stopped during the cycle. Accordingly, the nucleic acid extraction operation was not performed with respect to some samples, and a considerable number of samples were consumed.

Accordingly, a nucleic acid extraction device configured to redeem such problems and a method of operating the same are required.

DISCLOSURE

Technical Problem

The present invention is directed to providing a nucleic acid extraction device rotatively driven and configured to easily and safely extract nucleic acid from a solution sample and a method of operating the same.

It should be noted that objects of the present invention are not limited to the above-described objects, and other objects of the present invention will be apparent to those skilled in the art from the following descriptions.

Technical Solution

One aspect of the present invention provides a nucleic acid extraction device. The nucleic acid extraction device includes a container which stores each of a cleaning solution and an eluting solution, a water level sensor configured to detect amounts of the cleaning solution and the eluting solution which are stored in the container, a tube sensor configured to sense a sample tube disposed on a sample tube accommodation portion, and an operation initiation portion configured to determine whether the cleaning solution and the eluting solution which are necessary for a nucleic acid extraction operation are provided on the basis of the number of such sample tubes which is sensed by the tube sensor and the amounts of the cleaning solution and the eluting solution which are sensed by the water level sensor.

Specifically, the nucleic acid extraction device may further include a first rack on which a plurality of such sample tube accommodation portions are formed to be spaced apart along a perimeter, a second rack disposed below the first rack and on which a plurality of elution tube accommodation portions are formed to be spaced apart along a perimeter and cleaning solution accommodation portions are each formed between the plurality of elution tube accommodation portions along the perimeter, and a rotation-driving portion configured to rotate each of the first rack and the second rack. Here, the rotation-driving portion locates the sample tubes of the first rack above the cleaning solution accommodation portions or the elution tubes of the second rack and then performs the cleaning operation or the elution operation while rotating the first rack and the second rack.

Also, specifically, the tube sensor may sequentially sense whether the sample tubes are disposed on the sample tube accommodation portions, respectively, while rotating the first rack.

Also, specifically, the nucleic acid extraction operation may be performed for at least once every cycle, and the operation initiation portion may determine whether the cleaning solution and the eluting solution which are necessary for the nucleic acid extraction operation are provided for each cycle.

Also, specifically, the nucleic acid extraction device may further include a pressurizing portion which includes a pressurizing nozzle configured to transfer pressurized air to the sample tube, an elastic support portion connected to the pressurizing nozzle through an elastic member, and a vertical driving portion configured to vertically move the elastic support portion.

Also, specifically, the tube sensor may be implemented as a light sensor disposed to be adjacent to the pressurizing portion and may sense whether the pressurizing nozzle is present in a light path of the light sensor when the vertical driving portion moves the elastic support portion downward.

Also, specifically, the nucleic acid extraction device may further include a rack cap disposed on the second rack and including a plurality of through portions formed therein. Here, the plurality of through portions may be disposed to be spaced apart from each other along a perimeter and each thereof may cover the elution tube accommodation portion and the cleaning solution accommodation portion.

Also, specifically, the nucleic acid extraction device may further include a plurality of elution tubes accommodated in the elution tube accommodation portions of the second rack and each including a handle portion protruding outward.

Another aspect of the present invention provides a method of operating the nucleic acid extraction device. The method includes sensing amounts of a cleaning solution and an eluting solution which are stored in a container, sensing a sample tube disposed in a sample tube accommodation portion, determining whether the cleaning solution and the eluting solution which are necessary for a nucleic acid extraction operation on the basis of the number of such sample tubes and the amounts of the cleaning solution and the eluting solution are provided, and initiating the nucleic acid extraction operation when the cleaning solution and the elute are provided.

Specifically, the initiating of the nucleic acid extraction operation may include rotating and aligning a first rack and a second rack to allow the sample tubes accommodated on the first rack to be located above the cleaning solution accommodation portions of the second rack, in which a solution sample including nucleic acid and impurities is accommodated in the sample tube and the nucleic acid is absorbed by a filter member in the sample tube, performing a cleaning operation while synchronizing and rotating the first rack and the second rack, rotating and aligning the first rack and the second rack to allow the sample tubes accommodated on the first rack to be located above elution tubes of the second rack, and performing an elution operation while synchronizing and rotating the first rack and the second rack.

Also, specifically, the sensing of the sample tube may include sequentially sensing whether the sample tubes are disposed on the sample tube accommodation portions, respectively, while rotating the first rack.

Also, specifically, the nucleic acid extraction operation may be performed for at least once every cycle, and the sensing of the amounts of the cleaning solution and the eluting solution and the initiating of the nucleic acid extraction operation may be performed for each cycle.

Advantageous Effects

According to the present invention, since a rack is rotatively driven, motion components accompanied by nucleic acid extraction may be simplified so as to improve processing velocity, to reduce manufacturing costs, and to design for miniaturization.

Also, according to the present invention, the number of all sample tubes disposed on the rack may be easily checked by sensing each of the sample tubes while rotating the rack.

Also, according to the present invention, it is possible to prevent resources such as a sample and the like from being unnecessarily consumed by determining whether it is possible to perform a nucleic acid extraction operation while the rack is rotated on the basis of the number of the sample tubes and amounts of a cleaning solution and an eluting solution.

Also, according to the present invention, it is possible to eliminate contamination or interference between elution tube accommodation portions which are caused by the eluting solution and/or cleaning solution through aligned rotation and synchronized rotation of the rack.

Also, according to the present invention, since a nucleic acid extract is accommodated in an elute tube, it is possible to remove inconvenience of additionally pipetting nucleic acid for storage.

DESCRIPTION OF DRAWINGS

A brief description of the drawings will be provided to more fully understand the drawings referred to in the detailed description of the present invention.

MODES OF THE INVENTION

Figure 1A:
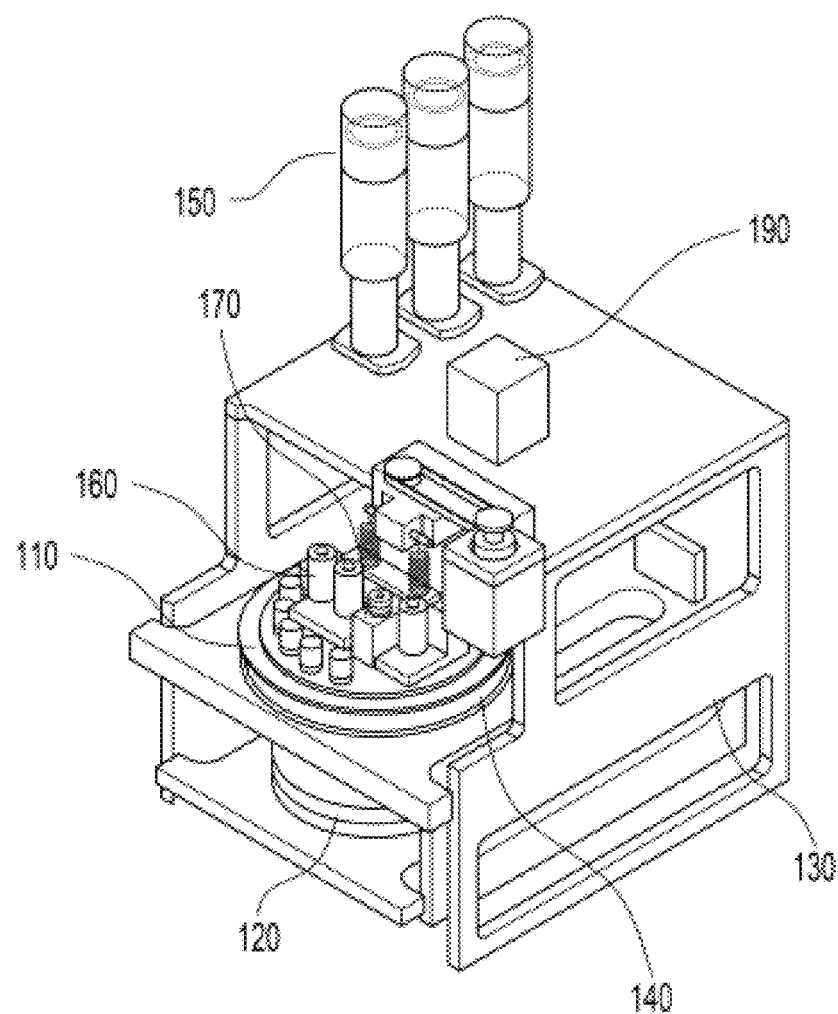
FIGS. 1A and 1B illustrate a nucleic acid extraction device according to one embodiment of the present invention.

Hereinafter, embodiments of the present invention will be described with reference to the attached drawings. While reference numerals are given to components of each drawing, it should be noted that although shown in different drawings, like components will be referred to as like reference numerals if possible. Also, in a description of the embodiments of the present invention, a detailed description of well-known components or functions of the related art will be omitted when it is deemed to obscure understanding of the embodiments of the present invention. Also, although the embodiments of the present invention will be described below, the technical concept of the present invention is not limited or restricted thereto and a variety of modifications thereof may be made by one of ordinary skill in the art. Meanwhile, vertical and lateral directions which will be described below are on the basis of the drawings for convenience, and the scope of the present invention is not limited to the corresponding directions.

Throughout the specification, when a part is stated as being "connected" to another part, the part is not only "directly connected" but also "indirectly connected" to the other component with another device therebetween. Throughout the specification, when a portion is stated as "including" a component, unless defined particularly otherwise, it means that the portion may not exclude another component but may further include another component. Also, in describing components of the embodiments of the present invention, the terms such as first, second, A, B, (a), (b), and the like may be used. These terms are merely for distinguishing one element from another, and the essence, order, sequence, and the like of corresponding elements are not limited by the terms.

Figure 1B:
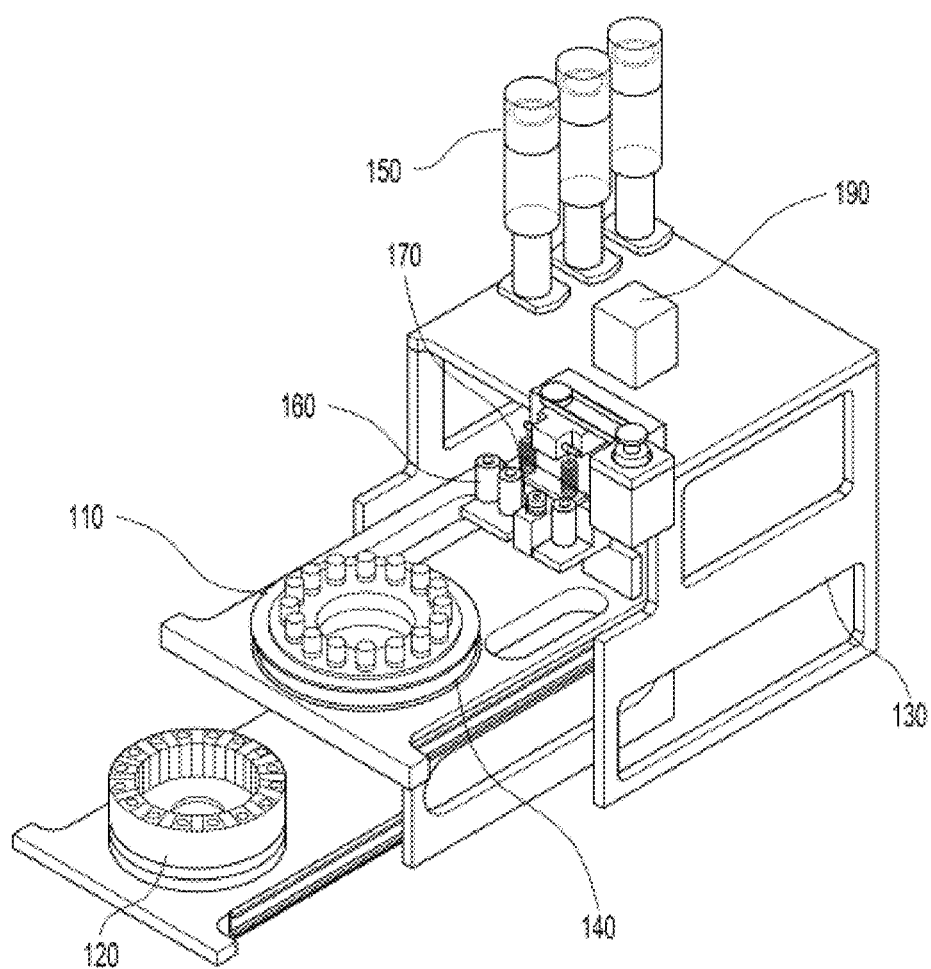
Figure 2A:
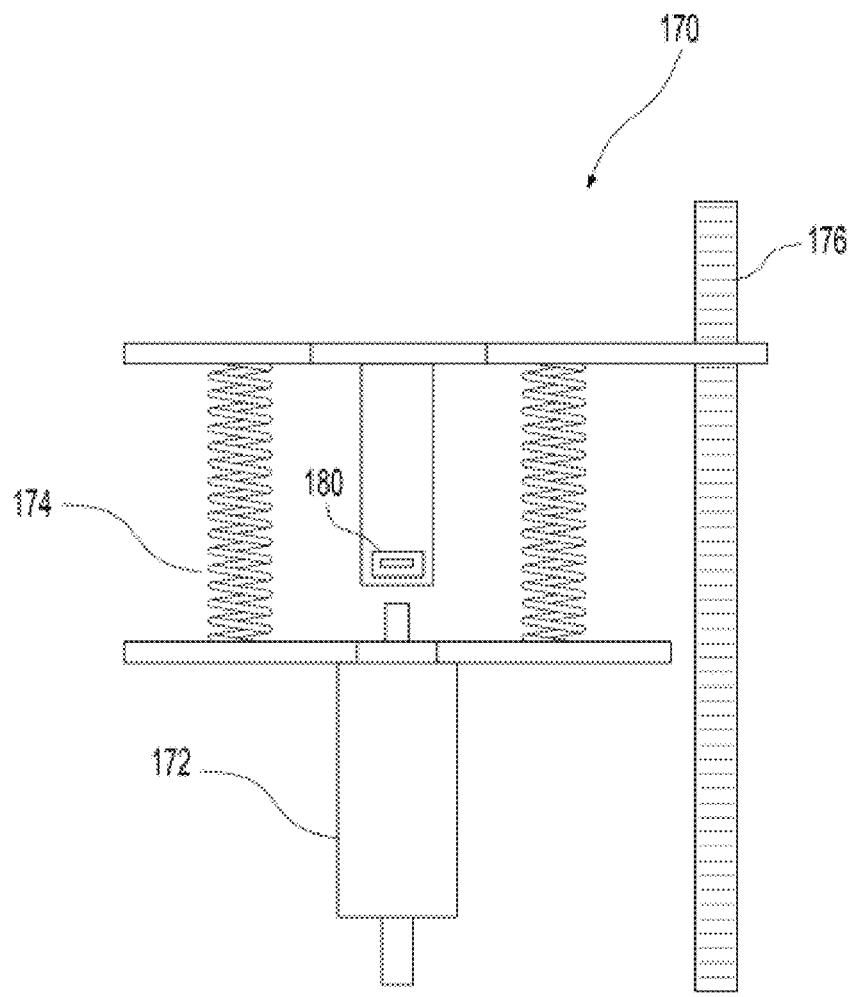
FIGS. 2A and 2B illustrate a pressurizing portion and a tube sensor according to one embodiment of the present invention.
Figure 2B:
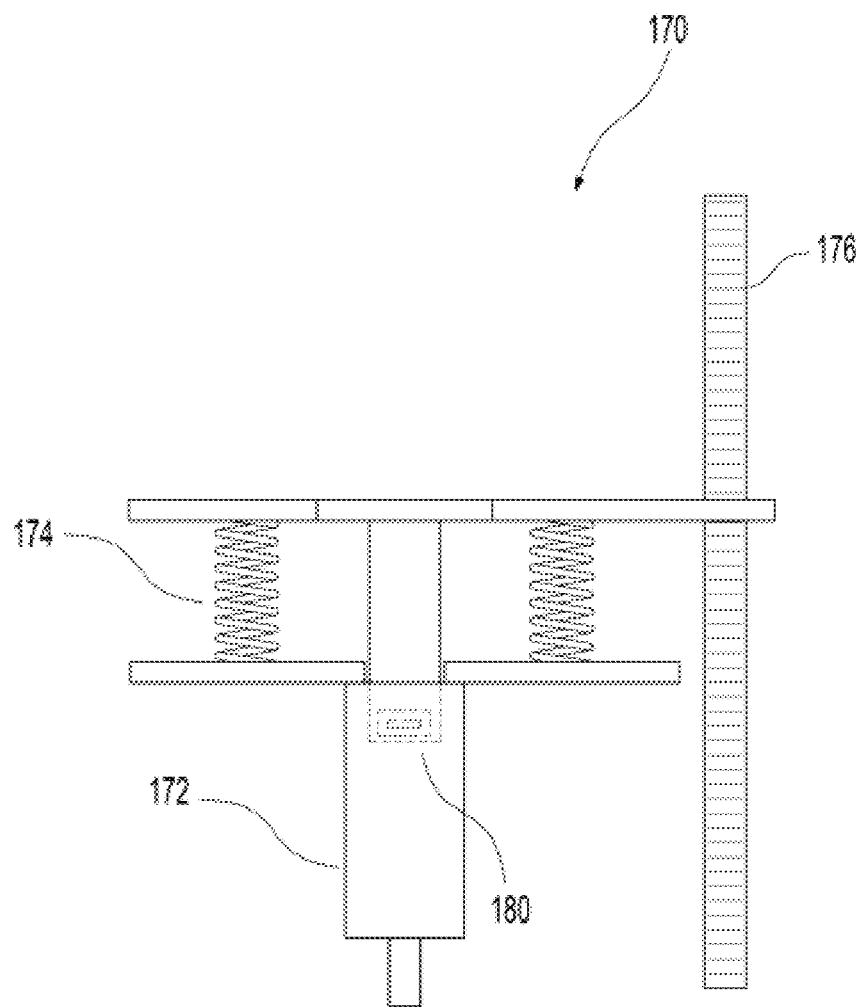
Figure 3:
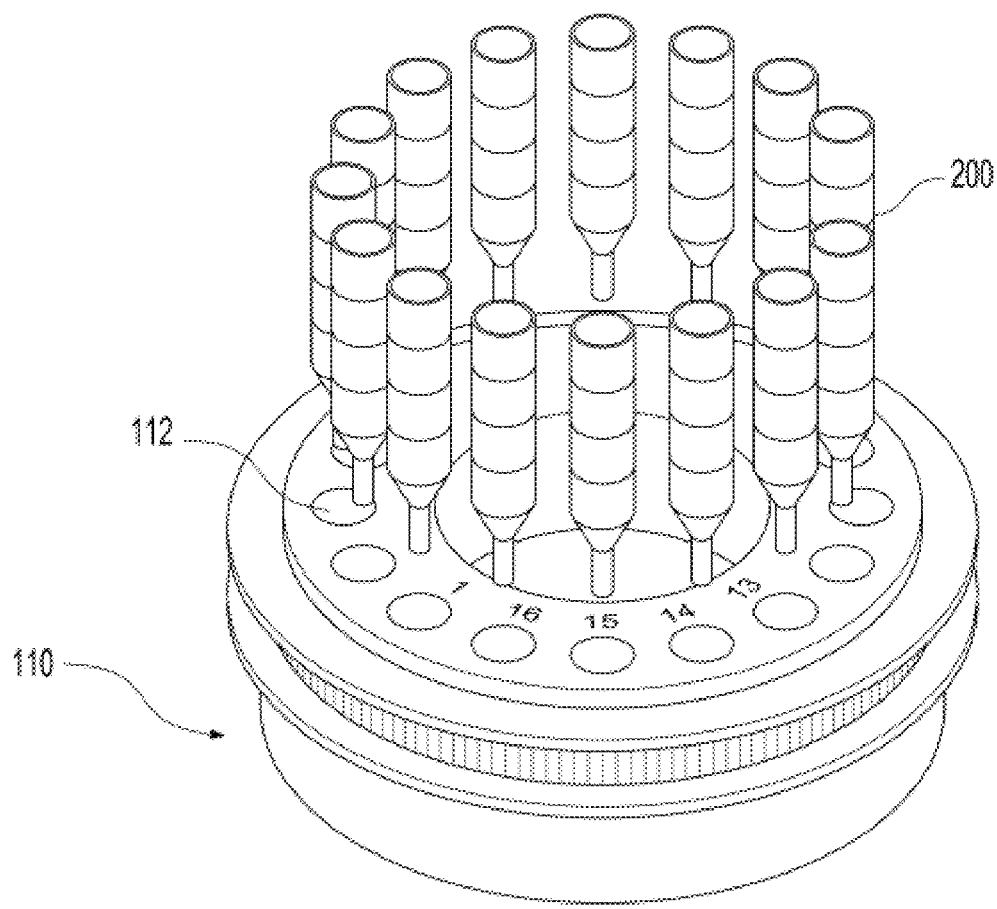
FIG. 3 illustrates a first rack of the nucleic acid extraction device according to one embodiment of the present invention.
Figure 4:
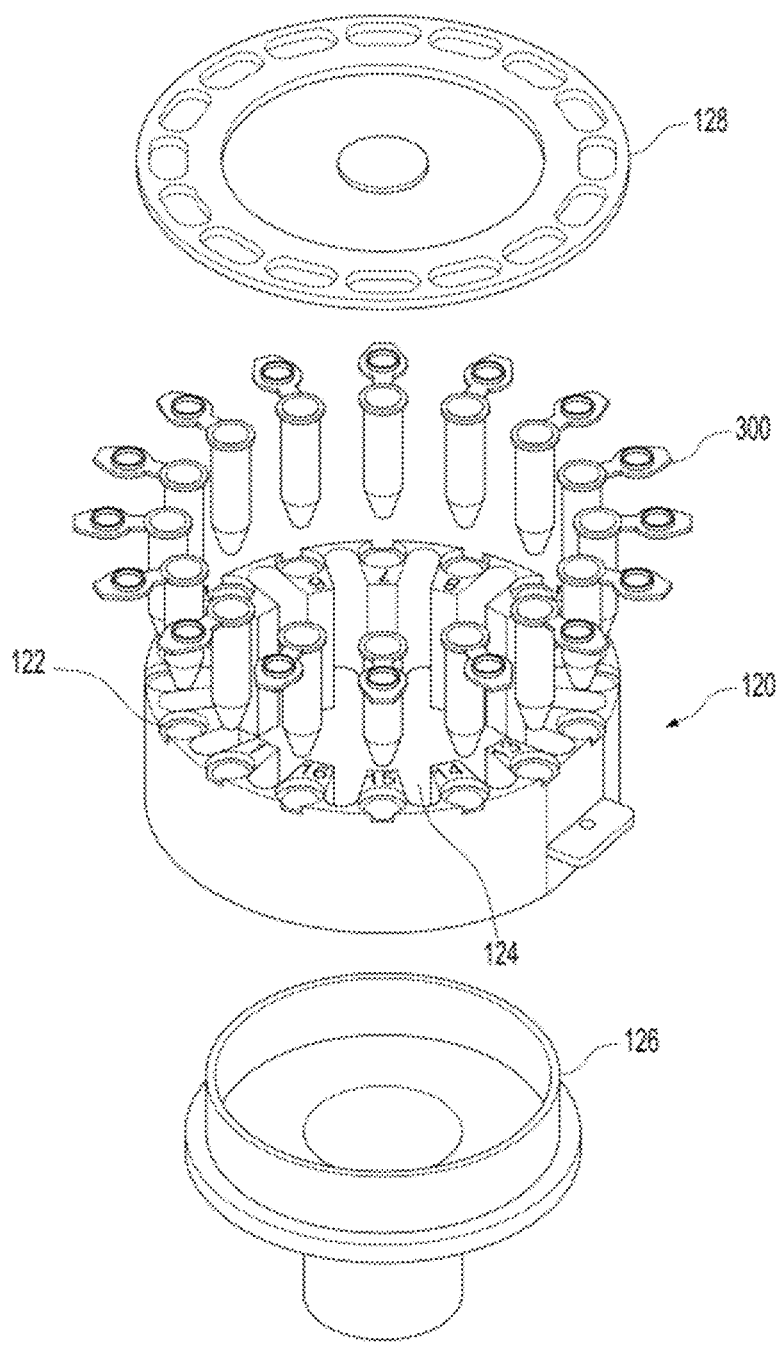
FIG. 4 illustrates a second rack of the nucleic acid extraction device according to one embodiment of the present invention.
Figure 5A:
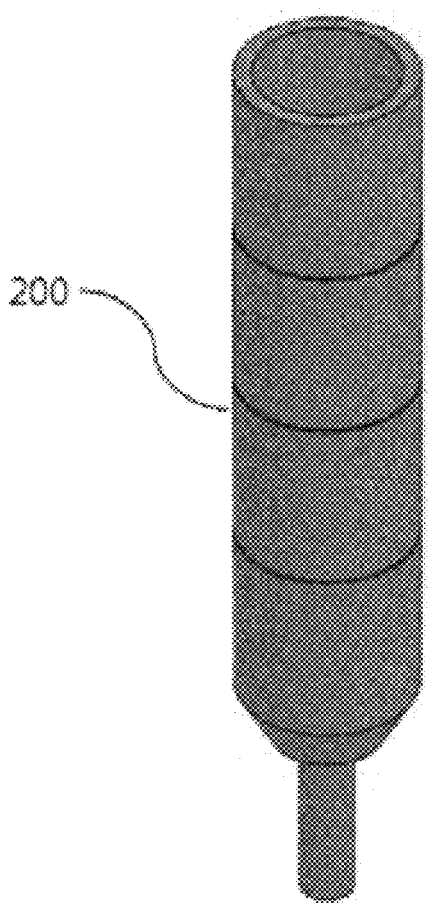
FIGS. 5A and 5B illustrate a sample tube according to one embodiment of the present invention.
Figure 5B:
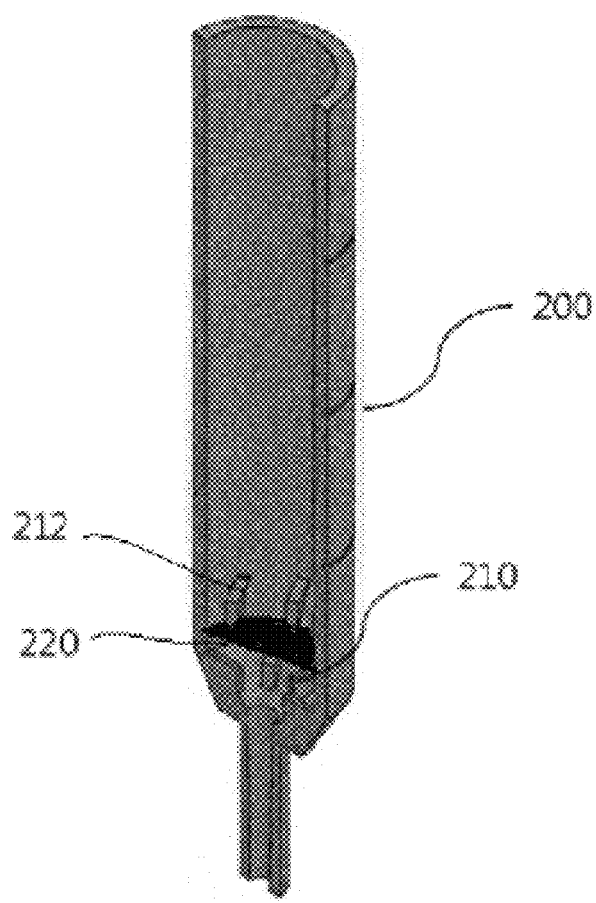

FIGS. 1A and 1B illustrate a nucleic acid extraction device according to one embodiment of the present invention, FIGS. 2A and 2B illustrate a pressurizing portion and a tube sensor according to one embodiment of the present invention, FIG. 3 illustrates a first rack of the nucleic acid extraction device according to one embodiment of the present invention, and FIG. 4 illustrates a second rack of the nucleic acid extraction device according to one embodiment of the present invention. FIGS. 5A and 5B illustrate a sample tube according to one embodiment of the present invention.

As shown in the drawings, the nucleic acid extraction device 100 may include a first rack 110, a second rack 120, a body 130, a rotation-driving portion 140, a container 150, a distributor 160, a pressurizing portion 170, a tube sensor 180, and an operation initiation portion 190.

The first rack 110 is configured to accommodate and fix a sample tube 200. To this end, a plurality of sample tube accommodation portions 112 configured to accommodate the sample tube 200 may be formed. The plurality of sample tube accommodation portions 112 may be spaced apart from each other and may have a circular shape along a perimeter of the first rack 110. Each of the sample tube accommodation portions 112 may be formed to accommodate the sample tube 200 and may include an opening portion at a bottom to transfer an extract from the sample tube 200 downward. Contamination or interference between the sample tubes 200 may be eliminated using a gap between the sample tube accommodation portions 112 and the sample tube accommodation portions 112 have a circular shape as described below in detail so as to allow an operation such as alignment and the like to be performed to extract nucleic acid only through rotation performed by the rotation-driving portion 140.

The sample tube 200 is configured to accommodate a solution sample and the like including nucleic acid and impurities and may have both ends which are open, particularly, while a lower end has an opening portion smaller than that of an upper end. Accordingly, it is possible to stably transfer an extract of the sample tube 200 to an elution tube 300 of the second rack 120 or a cleaning solution accommodation portion 124. Also, the sample tube 200 may include a filter support portion 210.

The filter support portion 210 is formed to protrude inward from one region inside the sample tube 200, particularly, a transition region having a decreasing cross section, and a filter member 220 may be disposed on the filter support portion 210 formed to protrude. Here, the filter member 220 is configured to adsorb nucleic acid, and include, for example, a porous membrane and the like. In addition, a filter fixing portion 212 may be additionally disposed above the filter member 220. The filter fixing portion 212 may fix a position and arrangement of the filter member 220 from above the filter member 220. As described above, the filter support portion 210 and the filter fixing portion 212 may support and fix the filter member 220 at the same time from above and below the filter member 220 so as to prevent degradation in filter performance caused by free movement of the filter or the like.

The second rack 120 is configured to accommodate and fix the elution tube 300 and to accommodate a cleaning solution at the same time and, to this end, may include an elution tube accommodation portion 122 and the cleaning solution accommodation portion 124.

The elution tube accommodation portion 122 is configured to accommodate and fix the elution tube 300. A plurality of such elution tube accommodation portions 122 may be spaced apart from each other and formed to have a circular shape along a perimeter of the second rack 120. Due to the gap between the elution tube accommodation portions 122, contamination or interference between the respective elution tube accommodation portions 122 caused by the extract from the sample tube 200 may be eliminated. Also, as described below in detail, the elution tube accommodation portion 122 may perform an operation such as alignment or the like for nucleic acid extraction only through rotation by the rotation-driving portion 140. The elution tube 300 accommodated in and fixed to the elution tube accommodation portion 122 is configured to accommodate nucleic acid extracted from the first rack 110 so that nucleic acid extracted from each of the sample tubes 200 may be separately accommodated and stored so as to eliminate inconvenience of transferring the extracted nucleic acid using an additional pipette or the like. Particularly, each of the elution tubes 300 may include a handle portion 310 protruding outward so as to be easily accommodated in and discharged from the elution tube accommodation portion 122. The elution tube accommodation portion 122 may include a certain groove at a position corresponding to the handle portion 310 to stably hold the handle portion 310.

The cleaning solution accommodation portion 124 is configured to accommodate a cleaning solution and may be formed at a center of the second rack 120 so that at least a part of the cleaning solution accommodation portion 124 is formed to protrude and extend outward so as to alternate with the plurality of elution tube accommodation portion 122. Since extending parts alternate with the plurality of elution tube accommodation portions 122 as described above, the operation of alignment or the like for accommodating the cleaning solution may be performed only through simple rotation by the rotation-driving portion 140.

A cleaning solution collection portion 126 is located at a bottom end of the second rack 120. The cleaning solution collection portion 126 is configured to collect the cleaning solution accommodated in the cleaning solution accommodation portion 124 of the second rack 120 and may be connected to one end of the cleaning solution accommodation portion 124 of the second rack 120 to communicate a fluid. In more detail, the cleaning solution accommodation portion 124 of the second rack 120 may include an opening portion in one region, and the cleaning solution or the like accommodated in the cleaning solution accommodation portion 124 may be discharged outward through the opening portion. The cleaning solution collection portion 126 may be located at a bottom end of the second rack 120 and may collect the cleaning solution or the like discharged through the opening portion of the cleaning solution accommodation portion 124. The cleaning solution collection portion 126 and the second rack 120 may be implemented to be detachably coupled so as to easily manage the nucleic acid extraction device 100 including collecting, discharging, and the like of the cleaning solution or the like by attaching or detaching the cleaning solution collection portion 126.

A rack cap 128 is configured to cover a top end of the second rack 120 and may include a plurality of through portions 129 spaced apart along a perimeter. Each of the through portions 129 may cover the elution tube accommodation portion 122 and the cleaning solution accommodation portion 124 at the same time. The rack cap 128 allows each of the through portions 129 to have a certain height so as to provide an effect of extending heights (or depths) of the elution tube accommodation portion 122 and the cleaning solution accommodation portion 124 of the second rack 120. Accordingly, for example, scattered matter of a fluid flowing into the cleaning solution accommodation portion 124 may be prevented from flowing into another adjacent elution tube 300.

The body 130 is a frame of the nucleic acid extraction device 100, and the first rack 110, the second rack 120, the rotation-driving portion 140, the distributor 160, the pressurizing portion 170, and the like may be disposed in the body 130. Particularly, in the body 130, the first rack 110 may be located above the second rack 120. Accordingly, the extract (nucleic acid or the like) from the sample tube 200 of the first rack 110 may be directly collected at the second rack 120.

Each of the first rack 110 and the second rack 120 may move horizontally with respect to the body 130. Here, movability horizontal to the body 130 may include direct movability horizontal to the body 130 and indirect movability horizontal to the body 130. As described above, since the first rack 110 and the second rack 120 are horizontally movable, the first rack 110 and the second rack 120 may be easily maintained and managed as well as easily accommodating and removing the sample tube 200, the elution tube 300, the first rack 110, the second rack 120, and the like to extract nucleic acid.

According to an embodiment, at least one of the first rack 110 and the second rack 120 may be detachably coupled to the body 130. That is, since at least one of the first rack 110 and the second rack 120 is implemented to be removable from the body 130, it is possible to easily use and manage the rack such as by mounting or demounting of a variety of tubes, discharging of the cleaning solution, and the like.

The rotation-driving portion 140 may be connected to each of the first rack 110 and the second rack 120 and rotate the first rack 110 and the second rack 120 simultaneously or separately. Rotation by the rotation-driving portion 140 may include single rotation of one of the first rack 110 and the second rack 120, aligned rotation of the first rack 110 and the second rack 120, synchronized rotation, and the like. For example, the single rotation is to rotate the first rack 110 or the second rack 120 separately and may be performed when the sample tube 200 accommodated in the sample tube accommodation portion 112 is sensed as described below. The aligned rotation may include rotating and aligning the first rack 110 and the second rack 120 to allow the sample tube 200 accommodated in the first rack 110 to be located above the cleaning solution accommodation portion 124 of the second rack 120 or rotating and aligning the first rack 110 and the second rack 120 to allow the sample tube 200 accommodated in the first rack 110 to be located above the elution tube 300 of the second rack 120. The above-described alignment is to change an accommodation portion of an extract depending on use of a cleaning solution or an eluting solution. The synchronized rotation means synchronizing rotation of the first rack 110 and the second rack 120 which are aligned by the aligned rotation. According to the synchronized rotation, since the first rack 110 and the second rack 120 rotate at the same time, relative positions of the sample tube 200 and the cleaning solution accommodation portion 124 or the sample tube 200 and the elution tube 300 are maintained equally. Simultaneously with the synchronized rotation, a cleaning solution or an eluting solution may be injected into the sample tube 200 of the first rack 110.

A plurality of such containers 150 may include at least one cleaning solution container which stores a cleaning solution and at last one eluting solution container which stores an eluting solution.

Each of the containers 150 may be connected to the distributor 160, and the distributor 160 may distribute a solution stored in each of the containers 150 into the sample tube 200.

A water level sensor (not shown) configured to sense a water level of a fluid stored in the container 150 may be disposed inside each of the containers 150. An amount of the cleaning solution or the eluting solution sensed by each water level sensor may be transferred to the operation initiation portion 190 and used to determine whether to initiate a nucleic acid extraction operation.

Although three containers 150 are shown in the drawing, the number of containers and the type of stored fluids may vary according to an embodiment to which the present invention is applied.

The distributor 160 may inject a certain fluid into the sample tube 200 through a distribution nozzle. The fluid is required for nucleic acid extraction and may include a cleaning solution, an eluting solution, and the like. In one embodiment, the distributor 160 may include an additional distribution nozzle for each fluid to prevent contamination between different fluids. In one embodiment, the distributor 160 may include a plurality of distribution nozzles configured to operate with respect to the plurality of sample tubes 200 at the same time so as to improve nucleic acid extraction velocity.

The distributor 160 may vertically move to be aligned with a position of the sample tube 200. In detail, the distributor 160 may vertically move to be rotated by the rotation-driving portion 140 to reduce a distance from the sample tube 200 located below the distributor 160 and to be pressed against the sample tube 200. Also, the distributor 160 may move horizontally. In detail, the distributor 160 may move toward the sample tube 200 for distribution or move horizontally to be farther away from the sample tube 200. The latter may include moving toward another sample tube 200 or separating from the corresponding sample tube 200 for pressurizing of the pressurizing portion 170. When a plurality of such distributors 160 are provided, the respective distributors 160 may horizontally and/or vertically move while being synchronized or may horizontally and/or vertically move separately.

The pressurizing portion 170 may pressurize an inside of the sample tube 200. To this end, the pressurizing portion 170 may include a pressurizing nozzle 172, an elastic support portion 174, and a vertical driving portion 176.

The pressurizing nozzle 172 may come into contact with the sample tube 200 and may inject pressurized air into the sample tube 200. Since the pressurized air is injected into the sample tube 200 by the pressurizing nozzle 172, the inside of the sample tube 200 may be pressurized so that at least a part of a fluid in the sample tube 200 may pass through the filter member in the sample tube 200 and may be extracted toward the second rack 120.

The elastic support portion 174 may connect the pressurizing nozzle 172 on a lower side to the vertical driving portion 176 on an upper side so as to transfer a driving force of the vertical driving portion 176 to the pressurizing nozzle 172. Here, the elastic support portion 174 is implemented as an elastic member such as a spring and the like and generates an elastic force toward the pressurizing nozzle 172 so that the pressurizing nozzle 172 may be pressed closely against the sample tube 200. When the pressurized air is injected into the sample tube 200 by being firmly pressed, a solution sample, a cleaning solution, an eluting solution, or the like in the sample tube 200 may be prevented from leaking outward due to pressurization.

The vertical driving portion 176 may be connected to the elastic support portion 174 and may vertically move the elastic support portion 174. The pressurizing nozzle 172 may be moved in a vertical direction through movement of the elastic support portion 174.

In one embodiment, the pressurizing portion 170 may include a plurality of such pressurizing nozzles 172 configured to operate with respect to the plurality of sample tubes 200 at the same time so as to improve nucleic acid extraction velocity.

The pressurizing portion 170 may move horizontally in addition to the vertical movement. In detail, the pressurizing portion 170 may move toward the sample tube 200 for pressurization or move horizontally to be farther away from the sample tube 200. The latter may include moving toward another sample tube 200 or separating from the corresponding sample tube 200 for distribution of the distributor 160. When a plurality of such pressurizing portions 170 are provided, the respective pressurizing portions 170 may horizontally and/or vertically move while being synchronized or may horizontally and/or vertically move separately.

The tube sensor 180 may sense the sample tubes 200 disposed in the sample tube accommodation portions 112 so as to check the number of the sample tubes 200 disposed on the first rack 110. The tube sensor 180 may be implemented, for example, as a light sensor or the like and may be disposed to be adjacent to the elastic support portion 174, the pressurizing nozzle 172, and the like and move in relation to the vertical driving portion 176. The tube sensor 180 may sense whether the pressurizing nozzle 172 is present in a light path. In a case in which the vertical driving portion 176 moves the elastic support portion 174 downward, when the sample tube 200 is not present below, the pressurizing nozzle 172 is not present in the light path (refer to FIG. 2A). Here, when the sample tube 200 is present below, since downward movement of the pressurizing nozzle 172 is blocked by the sample tube 200, the pressurizing nozzle 172 is present in the light path (refer to FIG. 2B).

As described above, the tube sensor 180 may sense whether the sample tube 200 is present below in relation to vertical movement of the vertical driving portion 176 and movement of the pressurizing nozzle 172. Particularly, to detect the number of all the sample tubes 200 disposed on the first rack 110, the sensing operation may be performed while the rotation-driving portion 140 rotates the first rack 110.

The operation initiation portion 190 may determine whether to initiate the nucleic acid extraction operation. When initiation is determined by the operation initiation portion 190, the nucleic acid extraction operation may be substantially performed. In detail, the operation initiation portion 190 may determine whether a cleaning solution and an eluting solution which are necessary for the nucleic acid extraction operation are provided on the basis of the number of the sample tubes 200 which is sensed by the tube sensor 180 and amounts of the cleaning solution and eluting solution which are sensed by the water level sensors. When adequate amounts of the cleaning solution and the eluting solution are provided, the nucleic acid extraction operation may be initiated.

In the present invention, the nucleic acid extraction operation may be performed for each of at least once every cycle. To this end, the operation initiation portion 190 may determine whether the cleaning solution and the eluting solution which are necessary for the nucleic acid extraction operation are provided for each cycle so that the rotation of the first rack 110 by the rotation-driving portion 140 and the vertical movement of the pressurizing portion 170 with respect to each of the sample tubes 200 and the sensing of the tube sensor 180 which are accompanied by the rotation may be performed for each cycle.

Figure 6:
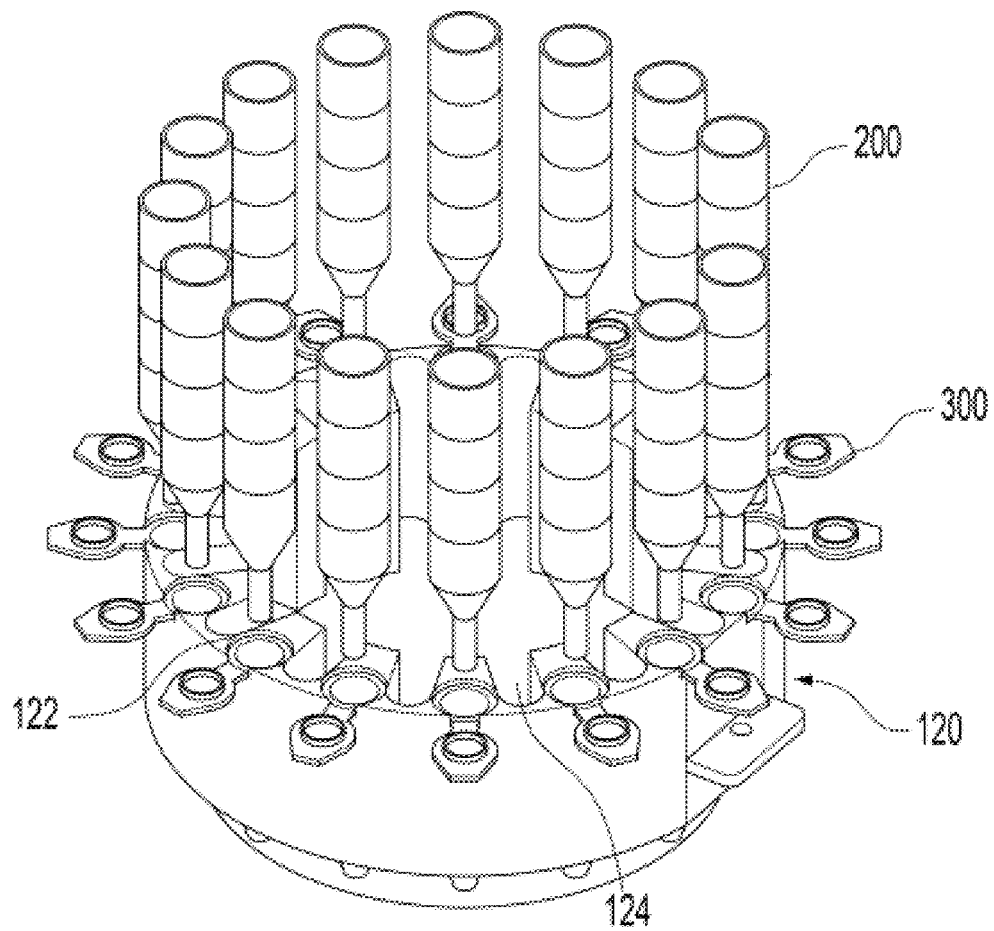
FIG. 6 illustrates an example of operations of the nucleic acid extraction device according to one embodiment of the present invention.

FIG. 6 illustrates an example of operations of the nucleic acid extraction device according to one embodiment of the present invention.

The rotation-driving portion 140 may rotate and align the first rack 110 and the second rack 120 to allow the sample tubes 200 of the first rack 110 to be located above the cleaning solution accommodation portion 124 of the second rack 120. Subsequently, since the rotation-driving portion 140 synchronizes and rotates the first rack 110 and the second rack 120, relative positions between the sample tube 200 of the first rack 110 and the cleaning solution accommodation portion 124 of the second rack 120 may be maintained equally. Simultaneously with synchronized rotation, the distributor 160 may inject the cleaning solution into the sample tube 200, and the pressurizing portion 170 may pressurize the inside of the sample tube 200. Accordingly, a cleaning operation may be performed with respect to each of the respective sample tubes 200 disposed on the first rack 110 sequentially.

That is, in the present invention, after rotation and alignment, injection of the cleaning solution and pressurization may be continuously performed with respect to a plurality of samples through synchronized rotation.

Figure 7:
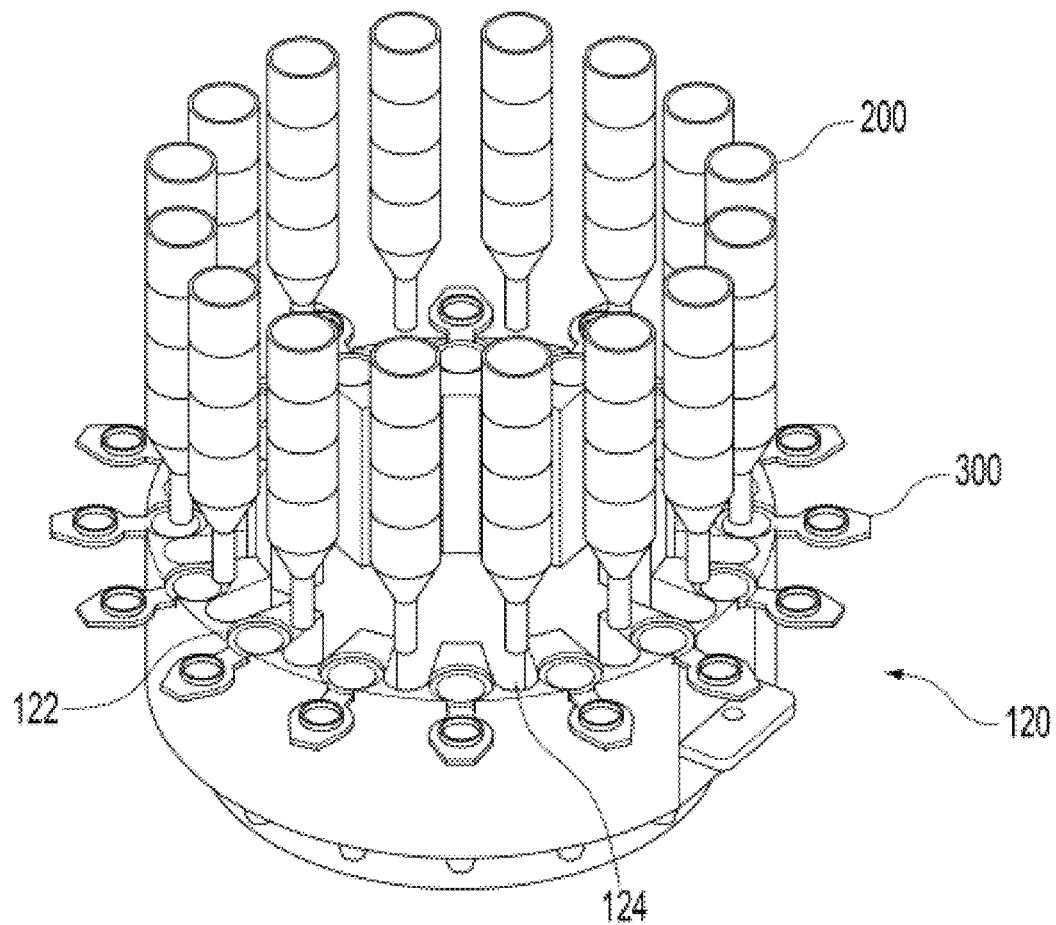
FIG. 7 illustrates an example of operations of the nucleic acid extraction device according to one embodiment of the present invention.

FIG. 7 illustrates an example of operations of the nucleic acid extraction device according to one embodiment of the present invention.

The rotation-driving portion 140 may rotate and align the first rack 110 and the second rack 120 to allow the sample tubes 200 of the first rack 110 to be located above the elution tubes 300 of the second rack 120. Subsequently, since the rotation-driving portion 140 synchronizes and rotates the first rack 110 and the second rack 120, relative positions between the sample tube 200 of the first rack 110 and the elution tube 300 of the second rack 120 may be maintained equally. Simultaneously with synchronized rotation, the distributor 160 may inject the eluting solution into the sample tube 200, and the pressurizing portion 170 may pressurize the inside of the sample tube 200. Accordingly, an elution operation may be performed with respect to each of the respective sample tubes 200 disposed on the first rack 110 sequentially.

That is, in the present invention, after rotation and alignment, injection of the eluting solution and pressurization may be continuously performed with respect to a plurality of samples through synchronized rotation.

Figure 8:
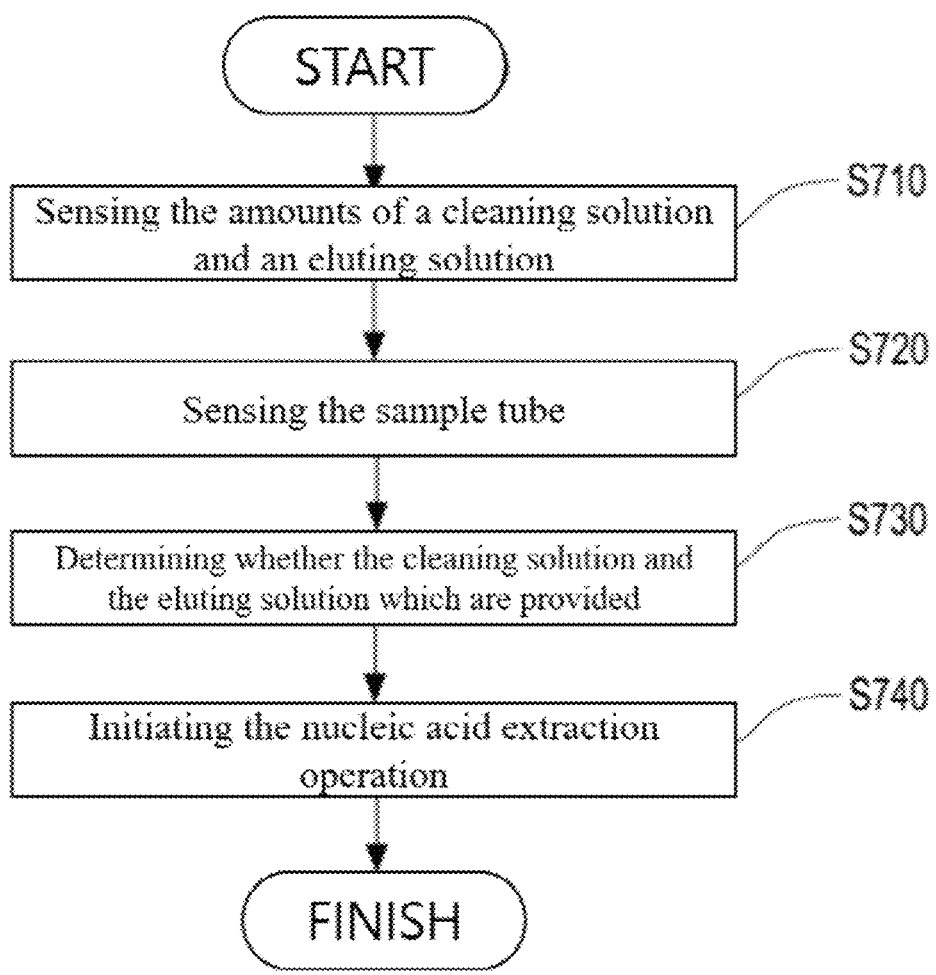
FIG. 8 illustrates a method of operating the nucleic acid extraction device according to one embodiment of the present invention.

FIG. 8 illustrates a method of operating the nucleic acid extraction device according to one embodiment of the present invention.

A method 700 is a process ahead of initiation of the nucleic acid extraction operation and is to determine whether an amount of a provided resource (cleaning solution, eluting solution, or the like) is adequate for performing the nucleic acid extraction operation.

First, in step S710, amounts of a cleaning solution and an eluting solution which are stored in the container 150 may be sensed. The step S710 may be performed by the water level sensor disposed in each container 150 but is not limited thereto, and a random value may be input by a user.

In step S720, the sample tube 200 disposed on the sample tube accommodation portion 112 may be sensed. The step S720 is to check the number of the sample tubes 200 disposed on the first rack 110 and may be performed by sensing whether the pressurizing nozzle 172 is present in the light path of the light sensor when the tube sensor 180 implemented as the light sensor is disposed to be adjacent to the elastic support portion 174 and the vertical driving portion 176 moves the elastic support portion 174 downward. Also, the step S720 may be performed on each of the sample tubes 200 while the rotation-driving portion 140 rotates the first rack 110.

In step S730, it may be determined whether the cleaning solution and the eluting solution which are necessary for the nucleic acid extraction operation are provided. The step S730 is performed by the operation initiation portion 190 and may be performed on the basis of the amounts of the cleaning solution/eluting solution which are sensed in the step S710 and the number of the sample tubes 200 which is sensed in the step S720.

When it is determined in the step S730 that adequate amounts of the cleaning solution and the eluting solution are provided, the nucleic acid extraction operation may be initiated in step S740. In the present invention, the nucleic acid extraction operation may be performed for at least once every cycle so that the method 700 may also be performed as a process ahead of the nucleic acid extraction operation for each cycle.

Figure 9:
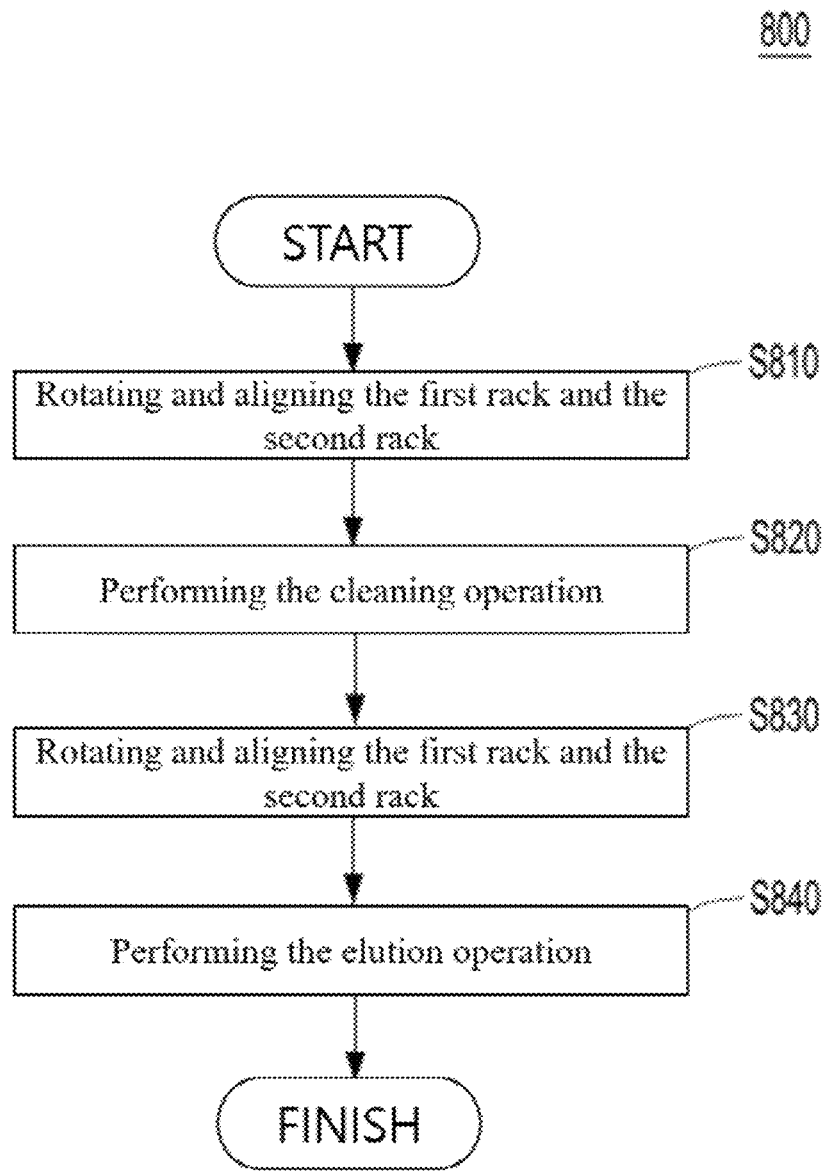
FIG. 9 illustrates a method of operating the nucleic acid extraction device according to one embodiment of the present invention.

FIG. 9 illustrates a method of operating the nucleic acid extraction device according to one embodiment of the present invention.

A method 800 of FIG. 9 is performed according to the step S740 of the method 700 of FIG. 8. First, in step S810, the first rack 110 and the second rack 120 may be rotated and aligned. The step S810 is to align positions of the first rack 110 and the second rack 120 to perform a cleaning operation with respect to the solution sample and, particularly, may be performed by the rotation-driving portion 140 rotating at least one of the first rack 110 and the second rack 120 to allow the sample tube 200 accommodated on the first rack 110 to be located above the cleaning solution accommodation portion 124 of the second rack 120 (refer to FIG. 6).

In step S820, the cleaning operation may be performed while the first rack 110 and the second rack 120 are synchronized and rotated. The step S820 may be performed by the rotation-driving portion 140 synchronizing and rotating the first rack 110 and the second rack 120, the distributor 160 injecting the cleaning solution into the sample tube 200, and the pressurizing portion 170 pressurizing the inside of the sample tube 200. Through the step S820, nucleic acid absorbed by the filter member may not be released by the cleaning solution and impurities may be released from the filter member by the cleaning solution so as to eliminate the impurities from a sample.

In step S830, the first rack 110 and the second rack 120 may be rotated and aligned. The step S830 is to align positions of the first rack 110 and the second rack 120 to perform an elution operation and, particularly, may be performed by the rotation-driving portion 140 rotating at least one of the first rack 110 and the second rack 120 to allow the sample tube 200 accommodated on the first rack 110 to be located above the elution tube 300 of the second rack 120 (refer to FIG. 7).

Finally, in step S840, the elution operation may be performed. The step S840 may be performed by synchronizing and rotating the first rack 110 and the second rack 120, injecting the eluting solution into the plurality of sample tubes 200, and pressurizing, by the pressurizing portion 170, the inside of the sample tube 200. Here, the eluting solution may release the nucleic acid absorbed by the filter member toward the elution tube 300 so that the extracted nucleic acid may be accommodated in the elution tube 300.

According to an embodiment, at least one of the step S820 and the step S840 may be performed a plurality of times, and a different cleaning solution or a different eluting solution may be used in each step.

As described above, optimum embodiments have been shown and described in the drawings and the specification. The particular terms used herein are merely intended to describe the present invention and are not used to limit the meanings or restrict the scope of the present invention disclosed in the claims. Therefore, it should be understood by one of ordinary skill in the art that a variety of modifications and equivalents thereof may be made. Accordingly, the technical scope of the present invention should be determined by the technical concept of the following claims.

The invention claimed is:

1. A nucleic acid extraction device comprising:
   a container storing each of a cleaning solution and an eluting solution;
   a water level sensor configured to detect amounts of the cleaning solution and the eluting solution which are stored in the container;
   a tube sensor configured to sense one or more sample tubes disposed on a plurality of sample tube accommodation portions;
   an operation initiation portion configured to determine whether the cleaning solution and the eluting solution which are necessary for a nucleic acid extraction operation are provided based on a number of the one or more sample tubes which is sensed by the tube sensor and the amounts of the cleaning solution and the eluting solution which are sensed by the water level sensor;
   a first rack on which the plurality of the sample tube accommodation portions are disposed to be spaced apart along a perimeter thereof;
   a second rack disposed below the first rack and on which a plurality of elution tube accommodation portions is disposed to be spaced apart along a perimeter thereof and a plurality of cleaning solution accommodation portions are each disposed between the plurality of elution tube accommodation portions along the perimeter thereof; and
   a rotation-driving portion configured to rotate each of the first rack and the second rack,
   wherein the rotation-driving portion positions the one or more sample tubes of the first rack above the plurality of cleaning solution accommodation portions or the plurality of elution tube accommodation portions of the second rack and performs a cleaning operation or an elution operation, respectively, while rotating the first rack and the second rack.

2. The nucleic acid extraction device of claim 1, wherein the tube sensor sequentially senses whether the one or more sample tubes are disposed on the plurality of sample tube accommodation portions, respectively, while rotating the first rack.

3. The nucleic acid extraction device of claim 1, wherein the nucleic acid extraction operation is performed for at least once every cycle, and
   wherein the operation initiation portion determines whether the cleaning solution and the eluting solution which are necessary for the nucleic acid extraction operation are provided for each cycle.

4. The nucleic acid extraction device of claim 1, further comprising a pressurizing portion which comprises:
   one or more pressurizing nozzles configured to transfer pressurized air to the one or more sample tubes;
   an elastic support portion connected to the one or more pressurizing nozzles through an elastic member; and
   a vertical driving portion configured to vertically move the elastic support portion.

5. The nucleic acid extraction device of claim 4, wherein the tube sensor is a light sensor disposed to be adjacent to the pressurizing portion and senses whether the one or more pressurizing nozzles is present in a light path of the light sensor when the vertical driving portion moves the elastic support portion downward.

6. The nucleic acid extraction device of claim 1, further comprising a rack cap disposed on the second rack and comprising a plurality of through portions formed therein,
   wherein the plurality of through portions are disposed to be spaced apart from each other along a perimeter of the rack cap and each of the plurality of through portions is located above one of the plurality of elution tube accommodation portions or the plurality of cleaning solution accommodation portions.

7. The nucleic acid extraction device of claim 1, further comprising a plurality of elution tubes accommodated in the plurality of elution tube accommodation portions of the second rack,
   wherein each of the plurality of elution tubes comprises a handle portion protruding outward.

8. A method of operating a nucleic acid extraction device, the method comprising:
   sensing amounts of a cleaning solution and an eluting solution which are stored in a container;
   sensing flail one or more sample tubes disposed in a sample tube accommodation portion;
   determining whether the cleaning solution and the eluting solution which are necessary for a nucleic acid extraction operation are provided based on a number of the one or more sample tubes and the amounts of the cleaning solution and the eluting solution are provided; and
   initiating the nucleic acid extraction operation when the cleaning solution and the eluting solution are determined to be provided,
   wherein the initiating of the nucleic acid extraction operation comprises:
   rotating and aligning a first rack and a second rack to allow the one or more sample tubes accommodated on the first rack to be located above cleaning solution accommodation portions of the second rack, in which a solution sample including nucleic acid and impurities is accommodated in the one or more sample tubes and the nucleic acid is absorbed by a filter member in the one or more sample tubes;
   performing a cleaning operation while synchronizing and rotating the first rack and the second rack;
   rotating and aligning the first rack and the second rack to allow the one or more sample tubes accommodated on the first rack to be located above elution tubes of the second rack; and
   performing an elution operation while synchronizing and rotating the first rack and the second rack.

9. The method of claim 8, wherein the sensing of the one or more sample tubes comprises sequentially sensing whether the one or more sample tubes are disposed on the sample tube accommodation portion while rotating the first rack.

10. The method of claim 8, wherein the nucleic acid extraction operation is performed for at least once every cycle, and
    wherein the sensing of the amounts of the cleaning solution and the eluting solution and the initiating of the nucleic acid extraction operation are performed for each cycle.

11. A nucleic acid extraction device comprising:
    a container storing each of a cleaning solution and an eluting solution;
    a water level sensor configured to detect amounts of the cleaning solution and the eluting solution which are stored in the container;
    a tube sensor configured to sense one or more sample tubes disposed on a plurality of sample tube accommodation portions;
    an operation initiation portion configured to determine whether the cleaning solution and the eluting solution which are necessary for a nucleic acid extraction operation are based on a number of the one or more sample tubes which is sensed by the tube sensor and the amounts of the cleaning solution and the eluting solution which are sensed by the water level sensor; and
    a pressurizing portion, wherein the pressuring portion comprises:
    one or more pressurizing nozzles configured to transfer pressurized air to the one or more sample tubes;
    an elastic support portion connected to the one or more pressurizing nozzles through an elastic member; and
    a vertical driving portion configured to vertically move the elastic support portion.

12. The nucleic acid extraction device of claim 11, wherein the tube sensor is a light sensor disposed to be adjacent to the pressurizing portion and senses whether the one or more pressurizing nozzles is present in a light path of the light sensor when the vertical driving portion moves the elastic support portion downward.

* * * * *